United States Patent [19]

Hirvonen et al.

[11] Patent Number: 4,482,250
[45] Date of Patent: Nov. 13, 1984

[54] METHOD FOR IDENTIFYING TIMBER SURFACE PROPERTIES

[75] Inventors: Kullervo Hirvonen; Aimo Karonen, both of Varkaus, Finland

[73] Assignee: Altim Control Ky., Varkaus, Finland

[21] Appl. No.: 334,085

[22] Filed: Dec. 24, 1981

[30] Foreign Application Priority Data

Feb. 10, 1981 [FI] Finland .................................. 810371

[51] Int. Cl.³ .......................................... G01N 21/21
[52] U.S. Cl. ................................................. 356/369
[58] Field of Search ............... 356/364, 365, 366, 367, 356/369; 250/225

[56] References Cited

U.S. PATENT DOCUMENTS 3,060,793 10/1962 Wells ...................................... 356/369
3,807,868 4/1974 Simila ..................................... 356/369
3,992,571 11/1976 Garlick et al. ........................ 356/365

FOREIGN PATENT DOCUMENTS 116211 9/1980 Japan ..................................... 356/369

OTHER PUBLICATIONS

Ward et al., "Correlation of Visual Luster with Measured Reflectance of Cotton Fabrics", *Textile Research Journal*, vol. 35, No. 3, Mar. 1965.

Primary Examiner—R. A. Rosenberger
Attorney, Agent, or Firm—Bucknam and Archer

[57] ABSTRACT

A method for identifying timber surface properties by using linearly polarized light. The polarization plane of the incident radiation is selected according to the object. The intensity components $I_{min}$ and $I_{max}$ having perpendicular polarization planes of the scattered radiation are measured, where the polarization plane of the component $I_{max}$ is the same as that of the incident radiation. On the basis of the quantities $I_{min}$ and $$P = \frac{I_{max} - I_{min}}{I_{max} + I_{min}}$$

conclusions are drawn about the surface properties of the examined surface.

1 Claim, 7 Drawing Figures

METHOD FOR IDENTIFYING TIMBER SURFACE PROPERTIES

PRIOR ART STATEMENT

The nearest prior art of which we are aware is disclosed by the U.S. Pat. No. 3,807,868. As described in the specification of our patent application, the prior art method is not suitable for the classifying of timber.

The present invention relates to a method for identifying the surface properties of timber, of sawn timber and plywood in particular, when determining defects and quality.

Sawn timber and plywood products to be used for various purposes are classified according to the surface properties of the product. The most important factors affecting the quality (and the strength) are knots, rot, bluestain, rough edges, skewness of grains, grub passages and mechanical defects. The price of board and plywood products is determined by quality classification.

The methods used today for determining timber surface properties or defects are based on tracing the intensity plane of radiation scattered from or gone through the surface to which electromagnetical radiation is directed by means of special geometrical arrangements. Depending on the radiation source, various light and radiation detectors as well as video and diode matrice cameras have been used for the detection. When cameras are used, image processing and pattern recognition algorithms setting great demands on computer capacity are often resorted to. In order to trace different defects, several wavelengths as well as different wavelength filters have been used in connection with the detectors and the cameras.

Specially suitable radiation sources for examining surfaces are lasers which yield a strong, monochromatic, collimated, coherent and often linearly polarized beam of light. It is easy to deviate a laser beam so that the entire surface to be examined can be analysed. A laser beam can also be focused into a very small spot, which enables also the examining of small surface parts having a size of about a micrometer.

The present invention is based on the utilisation of depolarization and a certain intensity component ensuing when linearly polarized radiation of the optical frequency area is scattered from a timber surface.

Depolarization and polarization occurring in connection with scattering were as phenomena known already in 19th century. Especially after lasers were developed (in the 1960's) a lot of research has been carried out concerning the effect of surface properties upon the parameters of scattered radiation. Corresponding research into the radio-frenquency area has a noticeably longer history.

Finnish Pat. No. 53365 discloses how the fibre direction of timber can be measured by means of polarized radiation of radio frequencies. In the present invention the frequency used as well as the equipment and method required are different.

U.S. Pat. No. 3,807,868 discloses a method for measuring the fibre orientation of paper, in which a polarized light beam is directed perpendicularly to the plane of the paper; the intensity of the scattered light is detected in two planes perpendicular to each other at a certain angle with regard to the paper plane so that two quantities are formed from the intensity of the light, one of which is obtained by conducting the scattered light to pass through a polarizer, the polarization plane of which is parallel to the polarization plane of the of the light beam and the other quantity is obtained by conducting the scattered light to pass through a polarizer the polarization plane of which is perpendicular to the polarization plane of the light beam; and in both planes the differences of the detected quantities are formed, the ratio and/or difference of which is used as the measure of the anisotropy of the fibre orientation of the object measured. This method cannot, however, be applied to in connection with timber. When classifying timber, the surface has to be examined entirely, e.g. by scanning it by means of a laser beam, to which situation the measuring arrangement disclosed in the patent in question can not be applied due to its detecting geometry and the processing of the signals. Furthermore, it has to be noted that in connection with timber, the depolarization phenomenon is not connected only to the fibre direction, as depolarizations caused by for example sound timber surface and a rotten timber surface differ from each other.

It is an object of the present invention to provide a method for accurate identification of diverse defects in timber surfaces and thus to enable the sorting of produced timber according to its quality.

The radiation scattered from the timber is diffused. Measurements carried out show that the defects met in timber (e.g. knots, rot, skewness of grains) cause depolarization which differs from that of sound timber and which can be used in a simple manner in the automatical identification of these defects. It is especially significant that the fibre orientation differing from sound timber shows up also in the depolarization (skewness of grains, transverse grains as well as the effect of a knot), which enables the use of the present method also in the strength measurement of timber.

The method according to the invention is characterized in that the timber surface to be examined is scanned by substantially monochromatic, collimated and linearly polarized radiation of the optical wavelength range, the polarization plane of which is parallel to the longitudinal direction of the timber or perpendicular to it and that from the scattered radiation the intensity components $I_{max}$ and $I_{min}$ having perpendicular polarization planes are measured, where the component's $I_{max}$ polarization plane is the same as that of the radiation coming to the surface. Conclusions about the surface properties are drawn by using the intensity component $I_{min}$ and the depolarization degree $$P = \frac{I_{max} - I_{min}}{I_{max} + I_{min}}.$$

The intensity component $I_{min}$ is much more applicable to the intensity plane comparisons than the conventionally used total reflection intensity which, when using the above symbols, is $$I = I_{max} + I_{min}.$$

The behaviour of the depolarization degree P is in one way connected with the fibre direction of the timber surface and in another way with the occurrance of certain defects such as rot. The physical reason for its behaviour is probably in the dielectric constant of timber, the value of which is different in the growth direction of timber and in the radial and tangential directions of the cross-section and which is also influenced by certain defects such as rot. Other reasons can be birefringence and optical activity. No explanatory theoretical models are, however, available—as a matter of fact the test results obtained may give impetus to new research activities.

The components $I_{max}$ and $I_{min}$ are measured from the radiation scattered from the surface by a method known per se using polarization filters or a prism that splits radiation into components (e.g. the Wollaston prism) as analysers.

Also when using cameras, the depolarization can be measured by placing the cameras so that the object is in the same position at their image plane and by using polarization filters in connection with their objectives as well as synchronously comparing the intensities of the image plane. Another possibility is to use the measuring device disclosed in the U.S. Pat. No. 3,992,571.

Different clauses can be used as a measure of depolarization, the most common of which is the above mentioned depolarization degree $$P = \frac{I_{max} - I_{min}}{I_{max} + I_{min}}$$

in which $I_{max}$ ($I_{min}$) is the maximum intensity (minimum intensity) given by the detector and obtained by rotating an analyser filter in front of the detector. The value of this clause is in the range between 0 (completely depolarized radiation) and 1 (linearly polarized radiation).

Depolarization depends to a noticeable degree upon the wavelength, for which reason the wavelengths used have to be selected on the basis of measurements of each application. Also the direction of the polarization plane of linearly polarized electromagnetical radiation directed to the surface has an effect on the results, wherefore its optimum direction should be determined by measurements.

In the measurements it has been found that the suitable wavelength for timber (sawn timber and plywood products) is 632.8 nm of a He Ne laser and that the most suitable direction of the polarization plane of the incident radiation is parallel to the growth direction of the wood. Then the light scattered from a sound timber surface is partly depolarized, whereas the light scattered from a knot is almost totally depolarized. Correspondingly, e.g. rot causes less depolarization than sound wood. According to the tests carried out, the method is suitable for examining both dry and moist wood.

Even the variations of the surface properties of sound timber are so great that the conventional tracing of the intensity plane I is not suited for the identification. On the other hand, it has been found that when linearly polarized radiation is used, the intensity component $I_{min}$ connected with the depolarization is applicable. It is hardly at all effected by e.g. the annual string structure (specular reflections which are present in the $I_{max}$ component), roughness of the surface or skewness of grains. The changes can be seen as a decrease in the intensity plane where there are defects (knots, rot, bluestain, cracks, grub passages etc.).

Another embodiment of the invention is to use the intensity component $I_{min}$ in intensity level comparisons, in which the basic level is the value of this component on sound or defectless surface.

By combining the intensity data thus obtained and the data about the depolarization degree of the scattered radiation, an identification method, is provided, one of the greatest advantages of which is that the required computer capacity is rather small.

When measuring only the intensity (e.g. I or $I_{min}$ component), the same measurement values are obtained for example such defects as rot, bluestain and knot, wherefor more data is required to support the conclusions drawn. This data is obtained e.g. by means of pattern recognition which requires a big computer capacity when applied to in practice.

By means of the depolarization degree, e.g. sound wood, rot and knots can be distinguished from each other, while strong skewness of grains and a knot come to the same class and e.g. sound wood, bluestain, discoloration and bark shake to the same class.

The present invention is based on the simultaneous use of the intensity component $I_{min}$ and the depolarization degree P. When comparing this method and the computer capacity it requires to the methods available on the market using pattern recognitions, it can be noted that there is decisively less need for both processing and memory storage.

The object to be examined must be illuminated with linearly polarized, usually relatively monochromatic light or radiation. Thus a polarizer has to be used in front of a normal source of light. Laser light is, depending on the type of laser, either naturally polarized or can easily be polarized. Furthermore, for examining the entire surface, there are systems suitable for 1- or 2-dimensioned deviation on the market. Taking into account the natural movement direction of plywood plates, 1-dimensioned deviation is sufficient for examining their surfaces. The most natural way to examine the surfaces of sawn timber is to move the timber in the longitudinal direction, but the method is not, however, limited to this case.

The invention is described in more detail in the following with reference to the accompanying drawings, in which FIG. 1 shows the principle of the equipment used in carrying out the method according to the invention;

Figure 1:
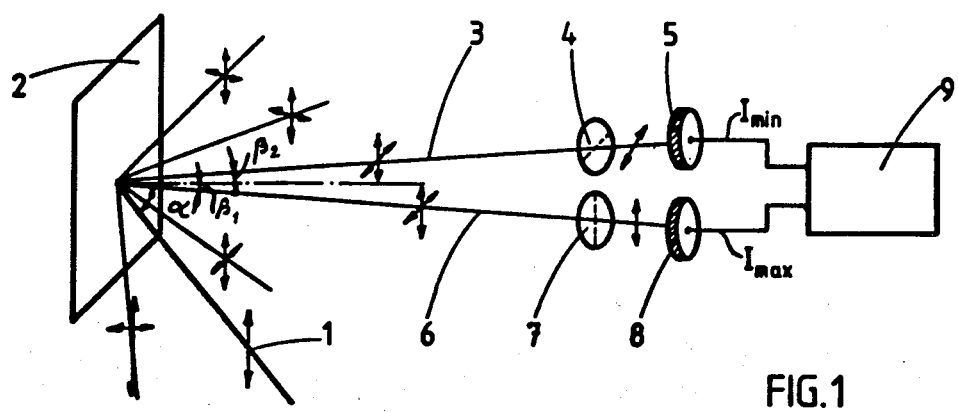

In the measurement device shown in FIG. 1, reference numeral 1 refers to a beam of light projected from a laser and directed towards the surface 2 of the object to be examined. The direction of the incident beam and the direction perpendicular to the surface form an angle α. Part 3 of the diffused scattered radiation passes through a polarization filter 4 to a detector 5 and part 6 through a polarization filter 7 to a detector 8. The measuring directions of the scattered radiation and the direction perpendicular to the surface form angles $\beta_1$ and $\beta_2$. The angles $\alpha, \beta_1, \beta_2$ are preferably about 15° at the most when measured in a plane parallel to the growth direction of the wood and about 50° at the most in the direction perpendicular to that plane.

The transmission directions of the polarizing filters are at an angle of 90° with each other in such a manner that the transmission direction of the detector 8 is parallel to the polarization plane of the incident radiation.

The intensity signals $I_{max}$ and $I_{min}$ are conducted to a processor 9 in which they are then, in a manner known per se, transformed to a form suitable for determining the quality of timber.

Figure 2:
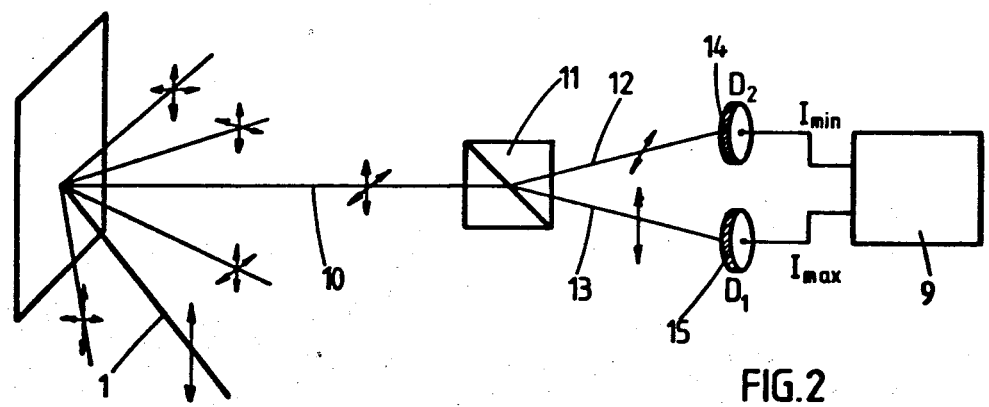
FIG. 2 shows an alternative embodiment.

In the alternative embodiment illustrated in FIG. 2, part 10 of the scattered radiation passes through a Wollaston prism 11 separated to polarization components 12 and 13 to detectors 14 and 15 which measure their intensities $I_{min}$ and $I_{max}$.

Figure 3:
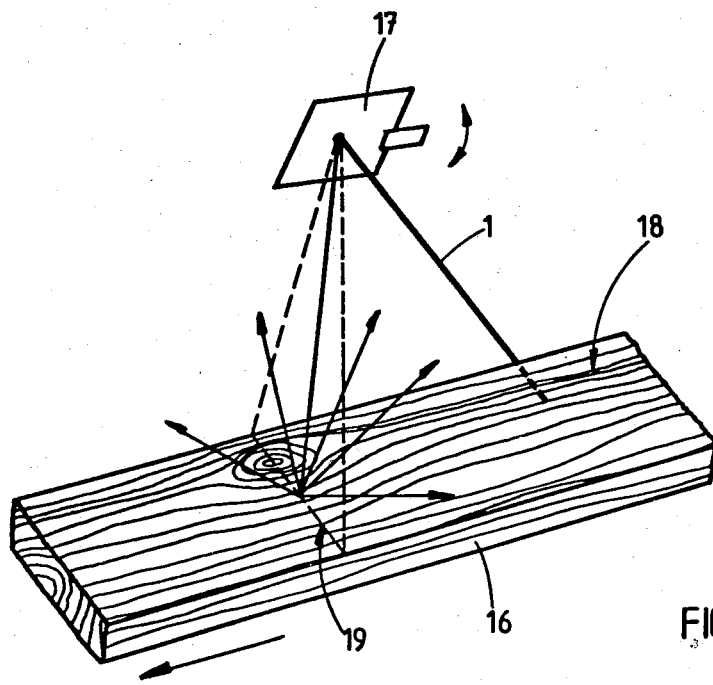
FIG. 3 is a simplified diagram illustrating the examining of the surface of sawn timber.
Figure 4:
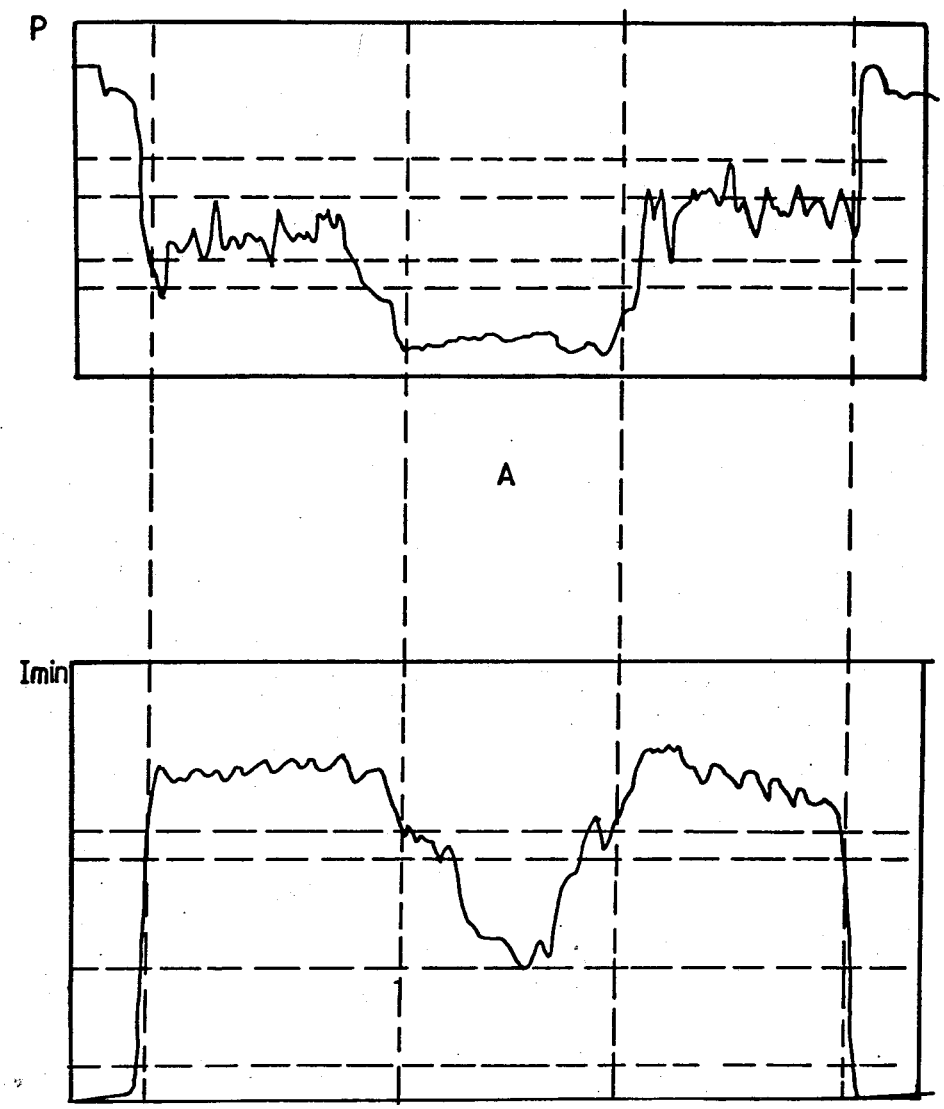
FIGS. 4 to 7 show some examples of the intensity curves obtained in the measurements of timber surfaces and of the corresponding curves showing the depolarization degree.
Figure 5:
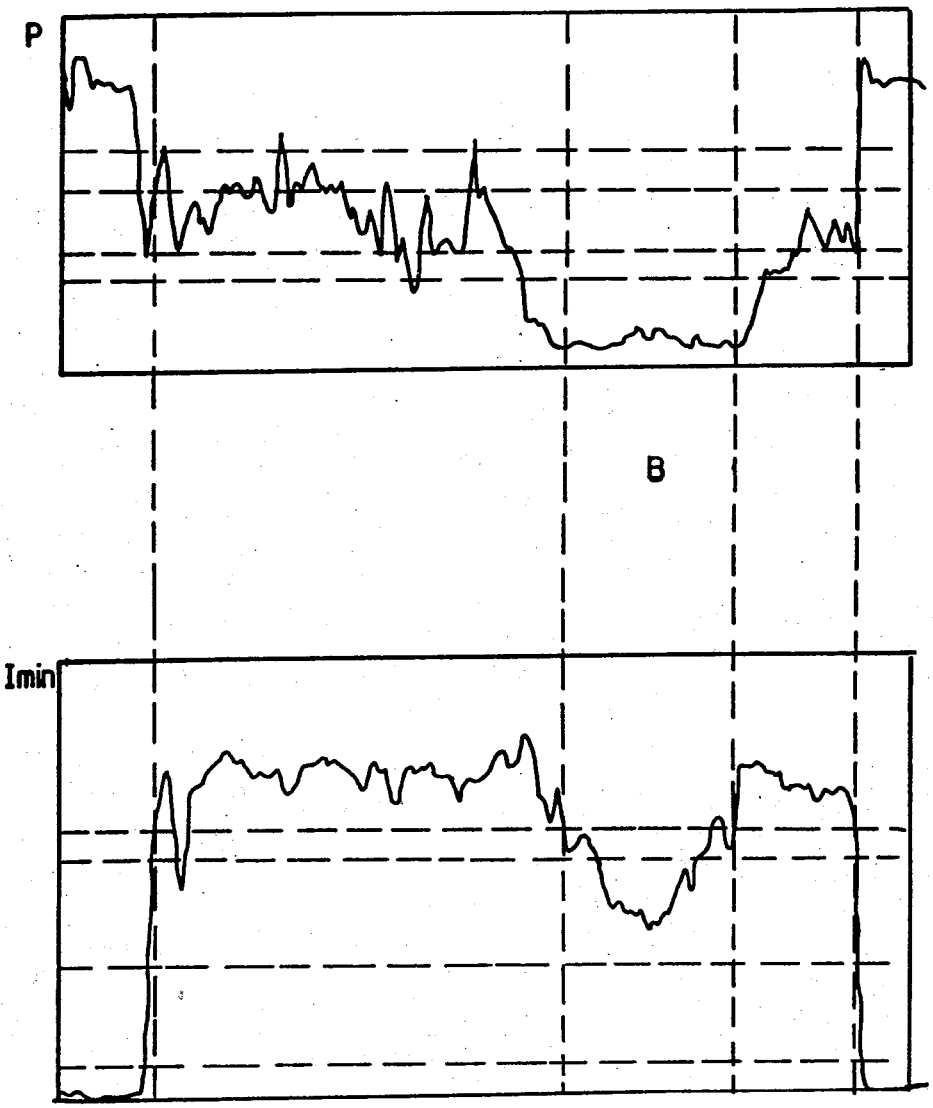
Figure 6:
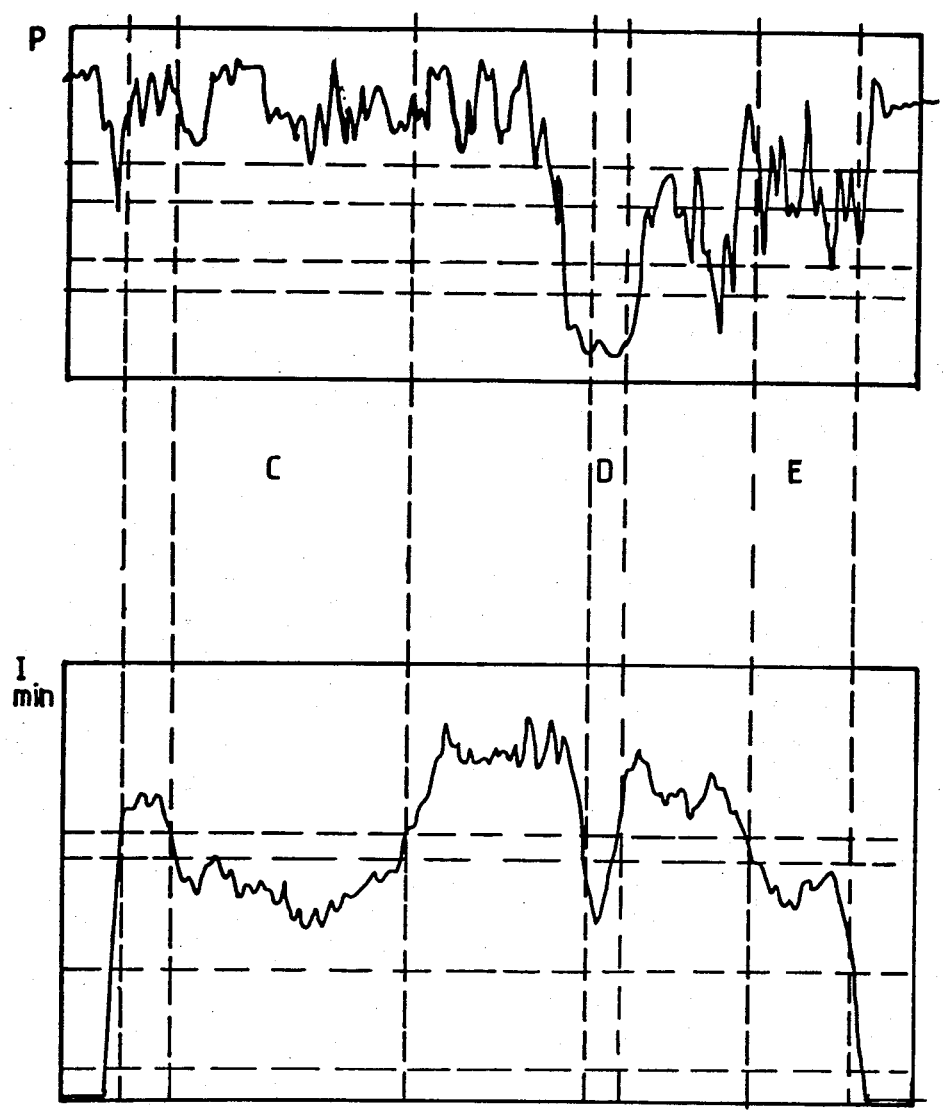
Figure 7:
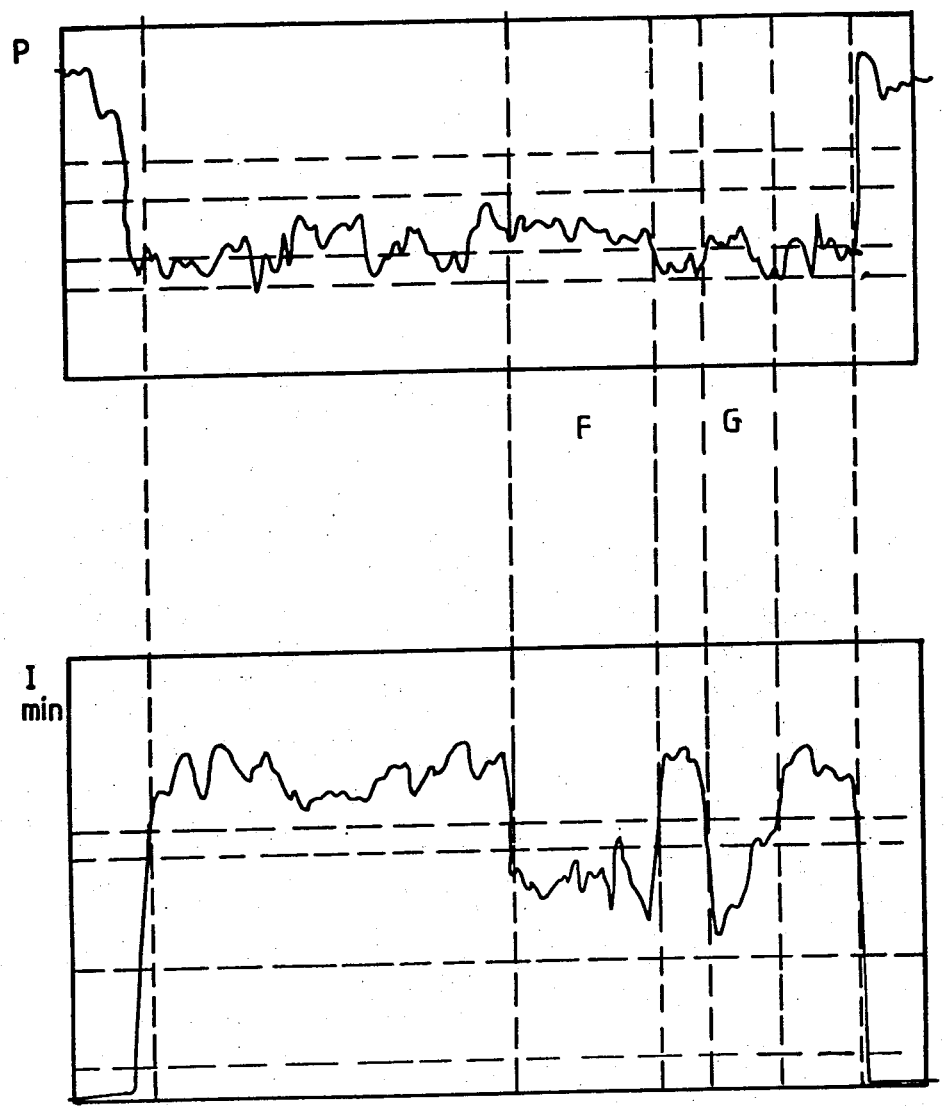

The principal arrangement of the equipment intended for examining a board is shown in FIG. 3. The light beam 1 is by means of a swivelling deviation mirror 17 caused to scan over a timber surface 18 in the cross direction of the board along a course 19. The board is moved in the longitudinal direction. The radiation scattered from the board surface is detected by the means according to FIG. 1 or 2.

EXAMPLES

FIGS. 4 to 7 show examples of single cross-scannings in which both sound timber surface and various typical defects can be seen. In the examples the depolarization degree and the intensity component $I_{min}$ are shown as a function of time time.

EXAMPLE 1 (FIG. 4)

A pine board having knots. Knot A can be seen in the picture as a decreased level of intensity and depolarization degree.

EXAMPLE 2 (FIG. 5)

A spruce board having knots. Knot B is seen in the same way as in the previous example. Spruce knots are usually slightly lighter, which can be seen as changes in the intensity. In the depolarization degree curve the knot is often somewhat wider than in the intensity curve. This is caused by the fact that the effect of the knot is seen even outside the actual knot as a change in the growth direction of the fibres. The growth direction of the fibres differs from the longitudinal direction of the tree and the method observes this.

EXAMPLE 3 (FIG. 6)

A rotten spruce board which has also a small knot. The intensity is decreased both in the knot D and the rot C and E, but the depolarization degree finally reveals what the defect is. In the knot the depolarization degree is very low, whereas in the rotten area it is higher than the average depolarization degree of sound wood.

EXAMPLE 4 (FIG. 7)

A pine board with bluestain. In the intensity curve the bluestain F and G is shown very similarly to rot, but the depolarization degree is clearly lower than for rotten wood and thus the rot and the bluestain can be distinguished.

We claim:

1. A method for determining timber surface properties, characterized in that substantially monochromatic, electromagnetical, linearly polarized radiation of the optical wavelength range is directed to the surface so that
    (a) the polarization plane of the radiation coming to the surface is either parallel to the growth direction of the wood or perpendicular to it,
    (b) the intensity components $I_{min}$ and $I_{max}$ having polarization planes of scattered radiation perpendicular to each other, are detected, wherein the polarization plane of the component $I_{max}$ is the same as the polarization plane of the incident radiation,
    (c) the quantities $I_{min}$ and $$P = \frac{I_{max} - I_{min}}{I_{max} + I_{min}}$$

are both used in determining the quality of the surface and further characterized in that the incoming direction of the incident radiation and measuring direction of the scattered radiation deviate from the direction perpendicular to the surface about 15° at the most when measured in a plane parallel to the longitudinal growth direction of the wood and about 50° at the most when measured in a plane perpendicular to the longitudinal growth direction of the wood.

* * * * *